(12) United States Patent
Latt et al.

(10) Patent No.: US 12,295,611 B2
(45) Date of Patent: May 13, 2025

(54) INFECTED-TISSUE EXTRACTION DEVICE AND METHODS OF USE THEREOF

(71) Applicant: Arizona Board of Regents on Behalf of the University of Arizona, Tucson, AZ (US)

(72) Inventors: L. Daniel Latt, Tucson, AZ (US); Carlos Urrea-De La Puerta, Tucson, AZ (US); Carolina Gomez Llanos, Tucson, AZ (US); Emilio Araiza, Tucson, AZ (US); Erick De Leon, Tucson, AZ (US); Eva Richter, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 270 days.

(21) Appl. No.: 18/310,529

(22) Filed: May 1, 2023

(65) Prior Publication Data
US 2023/0346419 A1    Nov. 2, 2023

Related U.S. Application Data

(60) Provisional application No. 63/337,145, filed on May 1, 2022.

(51) Int. Cl.
*A61B 17/3207* (2006.01)
*A61B 17/00* (2006.01)
*A61B 90/00* (2016.01)

(52) U.S. Cl.
CPC ............. *A61B 17/320708* (2013.01); *A61B 2017/00477* (2013.01); *A61B 2090/0813* (2016.02); *A61B 2217/005* (2013.01); *A61B 2217/007* (2013.01)

(58) Field of Classification Search
CPC ............. A61B 17/320708; A61B 2217/005
See application file for complete search history.

(56) References Cited

U.S. PATENT DOCUMENTS

| 3,670,732 | A | * | 6/1972 | Robinson | ....... A61B 17/320708 604/105 |
| 4,641,662 | A | * | 2/1987 | Jaicks | ................ A61B 10/0291 600/570 |
| 4,785,796 | A | * | 11/1988 | Mattson | ................ A61B 1/227 600/249 |
| 5,145,368 | A | * | 9/1992 | Tomic | ....................... A61C 5/40 433/91 |
| 5,348,023 | A | * | 9/1994 | McLucas | ........... A61B 10/0291 30/325 |
| 2004/0243157 | A1 | * | 12/2004 | Connor | ............... A61M 3/0283 606/159 |

* cited by examiner

*Primary Examiner* — Christian A Sevilla
(74) *Attorney, Agent, or Firm* — BLANK ROME LLP

(57) ABSTRACT

A device for removing infected tissue from a patient is provided. The device includes a handle body attached to a curette. The handle body comprises first and second channels extending therethrough. The curette comprises third and fourth channels extending therethrough. The first and third channels are disposed in fluid communication. The second and fourth channels are disposed in fluid communication. The curette comprises a generally cup-shaped curette head having a scraping edge at one end. The third and fourth channels comprise openings disposed proximate or within the curette head. Methods of using the device to remove infected tissue from a patient are disclosed.

18 Claims, 4 Drawing Sheets

10　　　　　　80　　　　　　30

INFECTED-TISSUE EXTRACTION DEVICE AND METHODS OF USE THEREOF

CROSS REFERENCE TO RELATED APPLICATIONS

This application claims the benefit of the filing date of U.S. Provisional Application No. 63/337,145, filed on May 1, 2022, entitled "INFECTED-TISSUE EXTRACTION DEVICE AND METHODS OF USE THEREOF." The entirety of the foregoing is hereby incorporated by reference.

FIELD OF THE INVENTION

The field of this invention generally relates to an improved method and apparatus for the nondestructive removal of cannulated surgical screws from patients.

BACKGROUND OF THE INVENTION

In 2017, approximately 22.3 million orthopedic surgeries were performed throughout the world. Certain common orthopedic surgeries (e.g., hip repair surgery, spinal vertebral fusion surgery) involve the use of screws to stabilize bones and/or bone fragments during the healing process. Post-operative complications, such as hardware failure and infection can occur at the surgical site. Follow-up surgery is often needed to remove loose hardware (e.g., bone screws) and infected tissue.

Devices, kits and methods of using same devices and kits are available to extract cannulated screws from bones at surgical sites. However, operators continue to encounter problems when attempting to extract cannulated screws from biological tissue (e.g., bone). Accordingly, there is still a need for improved devices and methods for extracting cannulated surgical screws.

DESCRIPTION

Definitions

Figure 1:
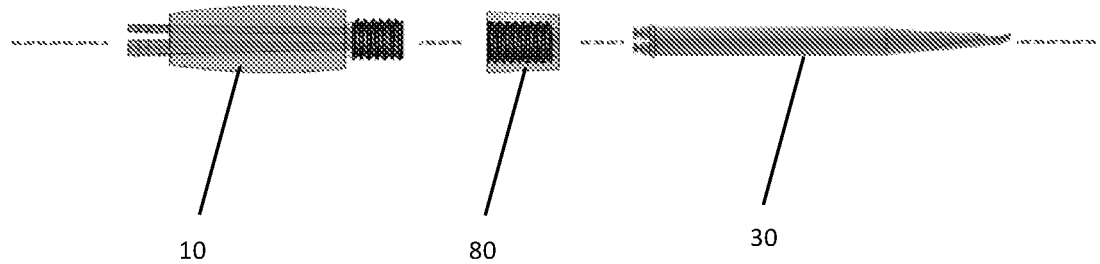
FIG. 1 is an exploded view, partially in section, of one embodiment of a device of the present disclosure of a device according to the present disclosure.

For the purposes of promoting an understanding of the principles of the invention, reference will now be made to certain embodiments and specific language will be used to describe the same. It will nevertheless be understood that no limitation of the scope of the invention is thereby intended, and alterations and modifications in the illustrated invention, and further applications of the principles of the invention as illustrated therein are herein contemplated as would normally occur to one skilled in the art to which the invention relates.

Unless defined otherwise, all technical and scientific terms used herein have the same meaning as commonly understood by one of ordinary skill in the art to which this invention pertains.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used).

The use of "or" means "and/or" unless stated otherwise.

The use of "a" or "an" herein means "one or more" unless stated otherwise or where the use of "one or more" is clearly inappropriate.

The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "about" refers to a ±10% variation from the nominal value. It is to be understood that such a variation is always included in any given value provided herein, whether or not it is specifically referred to.

As used herein, the term "biocompatible surface" refers to a surface of an object, the surface having the ability to be in contact with a patient without producing a substantial adverse effect on a tissue or biological system of the patient.

As used herein, the term "patient" refers to a mammalian organism (e.g., a human, a wild or domestic animal) being treated for a medical condition (e.g., a broken bone).

As used herein, the term "handle" refers to a part of an object that may be held, seized, or grasped.

As used herein, the term "cutting surface" refers to a surface whose profile is a decreasing angle configured for incising material without dulling.

As used herein, the term "manual force" refers to the effort exerted by the user of the apparatus to impart a force by way of mechanical advantage onto a fastener.

As used herein, the term "elastic material" refers to a material with a high elastic modulus and whose deformation is characterized in majority by elastic deformation.

As used herein, the term "cannula" refers to a tube for insertion into a vessel, duct, or cavity. During insertion its lumen is usually occupied by a trocar; following placement, the trocar is removed and the cannula remains patent as a channel for the flow of fluids.

As used herein, the term "cannulated" refers to an object that is defined by a cannula in its interior.

As used herein, the term "resilient" refers to a property of a substance or object which confers the ability of the substance or object to recoil or spring back into shape after bending, stretching, or being compressed. Optionally, the resilient property is facilitated by altering the temperature of the substance or object.

As used herein, the term "curette" refers to a curette is a surgical instrument designed for scraping or debriding biological tissue or debris in a biopsy, excision, or cleaning procedure. In form, the curette is a small hand tool, often similar in shape to a stylus; at the tip of the curette may be a small scoop, hook, or gouge.

The present disclosure generally relates to improved methods and devices for the removal of infected tissue from a patient. The devices of the present disclosure combine a curette for scraping and/or dislodging infected tissue with suction means and irrigation means into a single apparatus. The methods of the present disclosure are particularly useful for the removal of infected tissue disposed in and/or around a bone or a bone screw that is threadably engaged with a bone.

"Threadably engaged", as used herein, refers to screws or lag screws that are surrounded by tissue (e.g., bone tissue) that has enough integrity such that turning the threaded screw clockwise or counterclockwise relative to its longitudinal axis will result in movement of the screw along its longitudinal axis.

Advantageously, the devices of the present disclosure include features that permit the operator to use a single, optionally handheld, device to dislodge and remove tissue from an infected site in a patient. Moreover, the device optionally features exchangeable curettes, making it simple for an operator to adjust the dimensions of the scraping edge of the devices during the tissue-removal procedure. This aspect permits the operator to limit the exposure of adjacent healthy tissue to the mechanical scraping forces of the curette.

Figure 2:
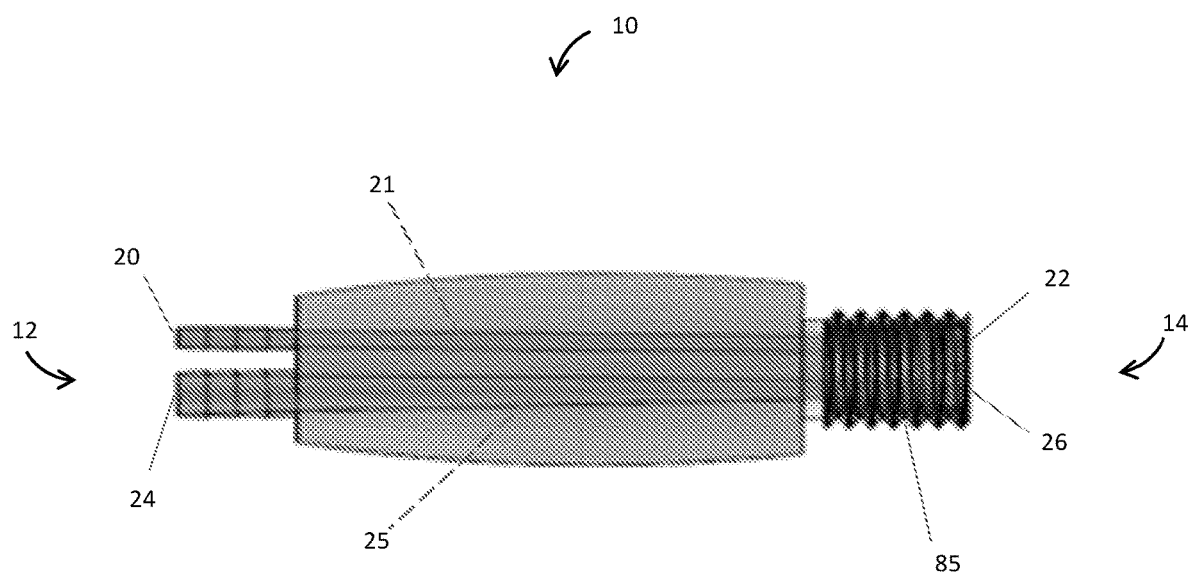
FIG. 2 is a plan view of the handle of the device of FIG. 1.

In one aspect, the present disclosure provides a device for extracting infected tissue (e.g., bone, soft tissue) from a patient (e.g., proximate a surgical wound or surgical repair site). FIG. 1 shows one embodiment of a device 100 according to the present disclosure. The device 100 comprises a handle body 10. FIG. 2 shows the handle body comprises a first end 12 and a second end 14. The first end 12 comprises a first opening 20 and a second opening 24. The second end 14 comprises a third opening 22 and a fourth opening 26.

The handle body 10 further comprises a first channel 21 extending therethrough from the first opening 20 to the third opening 22 and a second channel 25 extending therethrough from the second opening 24 to the fourth opening 26.

In any embodiment, the handle body 10 is adapted for manual grasping. Thus, in these embodiments, the handle body 10 is dimensioned to be grasped by two or more fingers and may be ergonomically shaped for operator comfort.

The first channel 21 and the second channel 25 are adapted for the transport of liquids (e.g., aqueous liquids such as water, a buffer solution) or liquid suspensions (e.g., an aqueous suspension of biological material such as cells or biological solids) In any embodiment, the handle body 10 can be constructed from a liquid-impermeable material (e.g., a metal, a polymer). Alternatively, the first channel 21 and the second channel 25 can be coated with a suitable liquid-impermeable coating.

The first channel 21 can be used to transport a liquid (e.g., sterile water, a sterile buffer) for irrigating tissue. Such liquids are well known in the art. The second channel 25 can be used to transport liquid suspensions of biological material, such as those suspensions generated by irrigating and/or scraping a wound site. Such suspensions can clog channels with solid debris. Thus, according to the present disclosure, the second channel 25 optionally tapers from the second opening 24 to the fourth opening 26, wherein the second opening is larger than the fourth opening, as illustrated in FIG. 2

Turning back to the Figures, the device 100 of FIG. 1 further comprises a curette 30 attached to the handle body 10. In any embodiment, the curette 30 can be detachably attached to the handle body 10.

Figure 3:
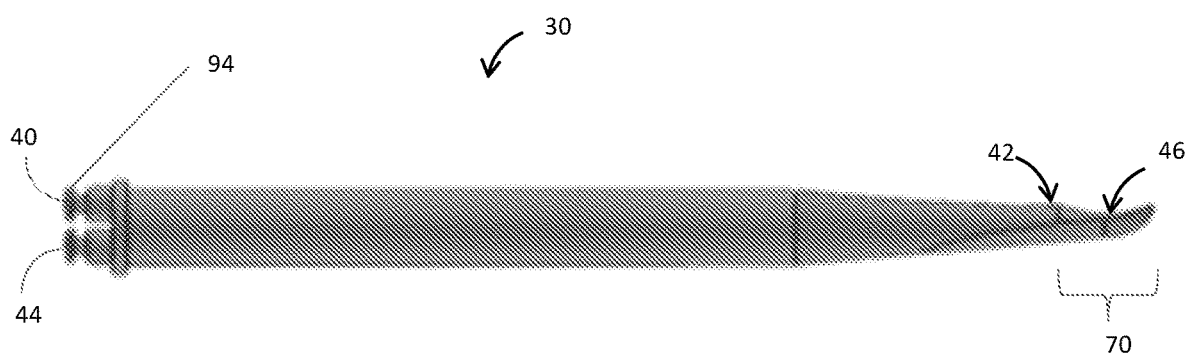
FIG. 3 is a plan view of the curette of the device of FIG. 1.

FIG. 3 shows the curette 30 comprises a third end 32 and a fourth end 34. The third end 32 comprises a fifth opening 40 and a sixth opening 44. The fourth end 34 comprises a generally cup-shaped curette head 70 having a scraping edge 72.

The curette 30 further comprises a seventh opening 42 and an eighth opening 46, both of which are individually located within or proximate the curette head 70. The curette 30 further comprises a third channel(not shown) extending therethrough from the fifth opening 40 to the sixth opening 42 and a fourth channel(not shown) extending therethrough from the seventh opening 44 to the eighth opening 46.

The third channel and the fourth channel are adapted for the transport of liquids (e.g., aqueous liquids such as water, a buffer solution) or liquid suspensions (e.g., an aqueous suspension of biological material such as cells or biological solids) In any embodiment, the handle body 10 can be constructed from a liquid-impermeable material (e.g., a metal, a polymer). Alternatively, the third channel and the fourth channel can be coated with a suitable liquid-impermeable coating.

In the fully-assembled device 10 (not shown), wherein the first opening 20 of the handle body 10 is in fluid communication with the seventh opening 42 of the curette 30 and the second opening 22 of the handle body 10 is in fluid communication with the eighth opening of the curette 30.

Figure 4:
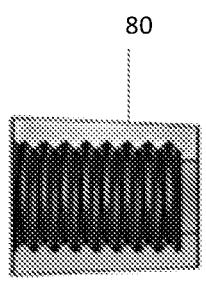
FIG. 4 is a cross-sectional view of the connector of FIG. 1.

The handle body can be attached (e.g., detachably attached) to the curette via a variety of means known in the art. In some embodiments (not shown), the handle body and the curette can be configured so that one of them can be press-fit or friction-fit into the other, for example. Alternatively, the device 100 of the present disclosure further can comprise a connector. In the illustrated embodiment of FIG. 1, the device 100 comprises a connector 80 adapted (e.g., threaded, as shown in FIG. 4) to connect the curette to the handle body (e.g., via a complementarily threaded connection structure 85 integral to the handle body 10).

Other connectors are contemplated including, but not limited to a friction-fit connector structure, a snap-fit connection structure, a magnet configured to apply a holding force, an adhesive, an interference fit, and a combination of any two or more of the foregoing connectors (not shown). In any embodiment, the curette is detachably attached to the handle body via the connector.

In any embodiment, a device 100 of the present disclosure further comprises an optional leak-resistant seal 92 disposed between the third opening 22 and the fifth opening 50, as shown, for example, in FIG. 3. In any embodiment, a device 100 of the present disclosure further comprises an optional leak-resistant seal 94 disposed between the fourth opening 26 and the seventh opening 44, as shown, for example, in FIG. 3.

The third channel (not shown) and the fourth channel(not shown) are adapted for the transport of liquids (e.g., aqueous liquids such as water, a buffer solution) or liquid suspensions (e.g., an aqueous suspension of biological material such as cells or biological solids) In any embodiment, the curette 30 can be constructed from a liquid-impermeable material (e.g., a metal, a polymer). Alternatively, the third channel and the fourth channel can be coated with a suitable liquid-impermeable coating.

The third channel can be used to transport a liquid (e.g., sterile water, a sterile buffer) for irrigating tissue. Such liquids are well known in the art. The fourth channel 25 can be used to transport liquid suspensions of biological material, such as those suspensions generated by irrigating and/or scraping a wound site. Such suspensions can clog channels with solid debris. Thus, according to the present disclosure, the fourth channel optionally tapers from the sixth opening 44 to the eighth opening 46, wherein the second opening is larger than the fourth opening, as illustrated in FIG. 2.

In any embodiment, the curette has a diameter that tapers proximate the curette head, as shown in FIG. 3. In any embodiment, the seventh opening (not shown) is disposed in the curette proximate the cup-shaped curette head. In any embodiment, the eighth opening is disposed in the cup-shaped curette head (not shown).

In any embodiment, a device of the present disclosure can be sterilized. In some embodiments, wherein the device is fabricated from materials that are not substantially degraded or deformed by exposure to steam up to 132° C. for a period of time sufficient to sterilize the device. In some embodiments, the device is fabricated from materials that are not substantially degraded or deformed by exposure to peroxide sterilant for a period of time and under conditions sufficient to sterilize the device. In some embodiments, the device is fabricated from materials that are not substantially degraded or deformed by exposure to ethylene oxide sterilant for a period of time and under conditions sufficient to sterilize the device. In some embodiments, the device is fabricated from materials that are not substantially degraded or deformed by exposure to ozone sterilant for a period of time and under conditions sufficient to sterilize the device.

In any embodiment, a portion of the scraping edge is crenate.

In another aspect, the present disclosure provides a method of removing infected tissue from a patient, the method comprising using any embodiment of the device of this disclosure to remove the infected tissue from the patient.

In any implementation, the method comprises scraping an infected site on or in the patient with the scraping edge of the curette head of any embodiment of the device of this disclosure to dislodge infected tissue at the infected site, flowing an irrigation liquid out of the seventh opening of the device to create a liquid suspension of the dislodged tissue, and applying a negative pressure to the eighth opening of the device to evacuate the liquid suspension from the infected site.

In any implementation of the method, flowing an irrigation liquid out of the seventh opening of the device can comprise adjusting the flow rate with a valve that is either integral with the device and is in fluid communication with the first channel or a valve that is in fluid communication with the device to the device.

In any implementation of the method, flowing an irrigation liquid out of the seventh opening of the device can comprise adjusting the flow rate with a valve that is either integral with the device and is in fluid communication with the first channel or a valve that is not integral with the device but is in fluid communication with the first channel device.

In any implementation of the method, applying a negative pressure to the eighth opening of the device to evacuate the liquid suspension comprises placing the second channel of the device in fluid communication with a source of negative pressure. In any implementation, the method further comprises adjusting the vacuum with a valve that is either integral with the device and is in fluid communication with the second channel or a valve that is not integral with the device but is in fluid communication with the second channel device.

In any implantation, the method further comprises detaching a first curette from the device and operatively attaching a second curette (e.g., with a curette head having a differently-dimensioned curette head than the first curette) to the device.

LIST OF EMBODIMENTS

Embodiment 1. A device, comprising:
a handle body comprising:
    a first end comprising first and second openings,
    a second end comprising third and fourth openings,
    a first channel extending through the handle body from the first opening to the third opening,
    a second channel extending through the handle body from the second opening to the fourth opening; and
a curette attached thereto, the curette comprising:
    a third end comprising fifth and sixth openings,
    a fourth end comprising a generally cup-shaped curette head having a scraping edge,
    seventh and eighth openings individually located within or proximate the curette head;
    a third channel extending through the curette from the fifth opening to the seventh opening, and
    a fourth channel extending through the curette from the sixth opening to the eighth opening;
wherein the first opening is in fluid communication with the seventh opening;
wherein the second opening is in fluid communication with the eighth opening.

Embodiment 2. The device of Embodiment 1, further comprising a connector that attaches the curette to the handle body.

Embodiment 3. The device of Embodiment 2, where the connector is selected from the group consisting of a friction-fit connector structure, a snap-fit connection structure, a threaded connection structure, a magnet configured to apply a holding force, an adhesive, an interference fit, and a combination of any two or more of the foregoing connectors.

Embodiment 4. The device of any one of Embodiments 1 through 3, wherein the curette is detachably attached to the handle body via the connector.

Embodiment 5. The device of any one of Embodiments 1 through 4, further comprising a leak-resistant seal disposed between the third opening and the fifth opening.

Embodiment 6. The device of any one of Embodiments 1 through 5, further comprising a leak-resistant seal disposed between the fourth opening and the sixth opening.

Embodiment 7. The device of any one of Embodiments 1 through 6, wherein the second channel tapers from the second opening to the fourth opening, wherein the second opening is larger than the fourth opening.

Embodiment 8. The device of any one of Embodiments 1 through 7, wherein the fourth channel tapers from the sixth opening to the eighth opening, wherein the sixth opening is larger than the eighth opening.

Embodiment 9. The device of any one of Embodiments 1 through 8, wherein the curette has a diameter that tapers proximate the curette head.

Embodiment 10. The device of any one of Embodiments 1 through 9, wherein the seventh opening is disposed in the curette proximate the cup-shaped curette head.

Embodiment 11. The device of Embodiment 10, wherein the eighth opening is disposed in the cup-shaped curette head.

Embodiment 12. The device of any one of Embodiments 1 through 11, wherein the device is fabricated from materials that are not substantially degraded or deformed by exposure to steam up to 132° C. for a period of time sufficient to sterilize the device.

Embodiment 13. The device of any one of Embodiments 1 through 11, wherein the device is fabricated from materials that are not substantially degraded or deformed by exposure to peroxide sterilant for a period of time and under conditions sufficient to sterilize the device.

Embodiment 14. The device of any one of Embodiments 1 through 11, wherein the device is fabricated from materials that are not substantially degraded or deformed by exposure to ethylene oxide sterilant for a period of time and under conditions sufficient to sterilize the device.

Embodiment 15. The device of any one of Embodiments 1 through 11, wherein the device is fabricated from materials that are not substantially degraded or deformed by exposure to ozone sterilant for a period of time and under conditions sufficient to sterilize the device.

Embodiment 16. The device of any one of Embodiments 1 through 15, wherein a portion of the scraping edge is crenate.

Embodiment 17. A method for removing infected tissue, wherein said method comprises using the device of any one of Embodiments 1 through 16 to remove infected tissue from a patient.

Embodiment 18. The method of Embodiment 17, wherein said infected tissue is removed by:
 scraping an infected site on or in the patient with the scraping edge of the curette head of the device of any one of Embodiments 1 through 16 to dislodge infected tissue at an infected site;
 flowing an irrigation liquid out of the seventh opening to create a liquid suspension of the dislodged tissue; and
 applying a negative pressure to the eighth opening to evacuate the liquid suspension from the infected site.

Embodiment 19. A kit comprising a handle body according to any one of Embodiments 1 through 16 and a plurality of curettes according to any one of Embodiments 1 through 16.

LIST OF EMBODIMENTS

In some embodiments the invention encompasses the following non-limiting list of embodiments:

1. A device, comprising:
 a handle body comprising:
  a first end comprising first and second openings,
  a second end comprising third and fourth openings,
  a first channel extending through the handle body from the first opening to the third opening,
  a second channel extending through the handle body from the second opening to the fourth opening; and
 a curette attached thereto, the curette comprising:
  a third end comprising fifth and sixth openings,
  a fourth end comprising a generally cup-shaped curette head having a scraping edge,
  seventh and eighth openings individually located within or proximate the curette head;
  a third channel extending through the curette from the fifth opening to the seventh opening, and
  a fourth channel extending through the curette from the sixth opening to the eighth opening;
 wherein the first opening is in fluid communication with the seventh opening;
 wherein the second opening is in fluid communication with the eighth opening.
2. The device of embodiment 1, further comprising a connector that attaches the curette to the handle body.
3. The device of embodiment 2, where the connector is selected from the group consisting of a friction-fit connector structure, a snap-fit connection structure, a threaded connection structure, a magnet configured to apply a holding force, an adhesive, an interference fit, and a combination of any two or more of the foregoing connectors.
4. The device of any one of embodiments 1 through 3, wherein the curette is detachably attached to the handle body via the connector.
5. The device of any one of embodiments 1 through 4, further comprising a leak-resistant seal disposed between the third opening and the fifth opening.
6. The device of any one of embodiments 1 through 5, further comprising a leak-resistant seal disposed between the fourth opening and the sixth opening.
7. The device of any one of embodiments 1 through 6, wherein the second channel tapers from the second opening to the fourth opening, wherein the second opening is larger than the fourth opening.
8. The device of any one of embodiments 1 through 7, wherein the fourth channel tapers from the sixth opening to the eighth opening, wherein the sixth opening is larger than the eighth opening.
9. The device of any one of embodiments 1 through 8, wherein the curette has a diameter that tapers proximate the curette head.
10. The device of any one of embodiments 1 through 9, wherein the seventh opening is disposed in the curette proximate the cup-shaped curette head.
11. The device of embodiment 10, wherein the eighth opening is disposed in the cup-shaped curette head.
12. The device of any one of embodiments 1 through 11, wherein the device is fabricated from materials that are not substantially degraded or deformed by exposure to steam up to 132° C. for a period of time sufficient to sterilize the device.
13. The device of any one of embodiments 1 through 11, wherein the device is fabricated from materials that are not substantially degraded or deformed by exposure to peroxide sterilant for a period of time and under conditions sufficient to sterilize the device.
14. The device of any one of embodiments 1 through 11, wherein the device is fabricated from materials that are not substantially degraded or deformed by exposure to ethylene oxide sterilant for a period of time and under conditions sufficient to sterilize the device.
15. The device of any one of embodiments 1 through 11, wherein the device is fabricated from materials that are not substantially degraded or deformed by exposure to ozone sterilant for a period of time and under conditions sufficient to sterilize the device.
16. The device of any one of embodiments 1 through 15, wherein a portion of the scraping edge is crenate.
17. A method for removing infected tissue, wherein said method comprises using the device of any one of embodiments 1 through 16 to remove infected tissue from a patient.
18. The method of embodiment 17, wherein said infected tissue is removed by:
 scraping an infected site on or in the patient with the scraping edge of the curette head of the device of any one of embodiments 1 through 16 to dislodge infected tissue at an infected site;
 flowing an irrigation liquid out of the seventh opening to create a liquid suspension of the dislodged tissue; and
 applying a negative pressure to the eighth opening to evacuate the liquid suspension from the infected site.

3.0 EXAMPLES

The following examples are provided solely to illustrate the present invention and are not intended to limit the scope of the invention, described herein.

Example 1. Construction of a Device for Removing Infected Tissue from a Patient

Components (handle body, curette, and the connector) of the illustrated device of FIG. 1 were fabricated using a 3-D printer. The material used to build the handle body and the connector was Nylon 12 (3D High Reusability PA 12 Glass Beads, obtained from Hewlitt-Packard). The material used to build the curette was Stainless Steel 316L.

All publications mentioned herein are incorporated by reference to the extent they support the present invention.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

We claim:

1. A device, comprising:
    a handle body comprising:
        a first end comprising first and second openings,
        a second end comprising third and fourth openings,
        a first channel extending through the handle body from the first opening to the third opening,
        a second channel extending through the handle body from the second opening to the fourth opening; and
    a curette attached thereto, the curette comprising:
        a third end comprising fifth and sixth openings,
        a fourth end comprising a generally cup-shaped curette head having a scraping edge,
        seventh and eighth openings individually located within or proximate the curette head;
        a third channel extending through the curette from the fifth opening to the seventh opening, and
        a fourth channel extending through the curette from the sixth opening to the eighth opening;
    wherein the first opening is in fluid communication with the seventh opening;
    wherein the second opening is in fluid communication with the eighth opening.

2. The device of claim 1, further comprising a connector adapted to attach the curette to the handle body.

3. The device of claim 2, where the connector is selected from the group consisting of a friction-fit connector structure, a snap-fit connection structure, a threaded connection structure, a magnet configured to apply a holding force, an adhesive, an interference fit, and a combination of any two or more of the foregoing connectors.

4. The device of claim 2, wherein the curette is detachably attached to the handle body via the connector.

5. The device of claim 1, further comprising a leak-resistant seal disposed between the third opening and the fifth opening.

6. The device of claim 1, further comprising a leak-resistant seal disposed between the fourth opening and the sixth opening.

7. The device of claim 1, wherein the second channel tapers from the second opening to the fourth opening, wherein the second opening is larger than the fourth opening.

8. The device of claim 1, wherein the fourth channel tapers from the sixth opening to the eighth opening, wherein the sixth opening is larger than the eighth opening.

9. The device of claim 1, wherein the curette has a diameter that tapers proximate the curette head.

10. The device of claim 1, wherein the seventh opening is disposed in the curette proximate the cup-shaped curette head.

11. The device of claim 10, wherein the eighth opening is disposed in the cup-shaped curette head.

12. The device of claim 1, wherein the device is fabricated from materials that are not substantially degraded or deformed by exposure to steam up to 132° C. for a period of time sufficient to sterilize the device.

13. The device of claim 1, wherein the device is fabricated from materials that are not substantially degraded or deformed by exposure to peroxide sterilant for a period of time and under conditions sufficient to sterilize the device.

14. The device of claim 1, wherein the device is fabricated from materials that are not substantially degraded or deformed by exposure to ethylene oxide sterilant for a period of time and under conditions sufficient to sterilize the device.

15. The device of claim 1, wherein the device is fabricated from materials that are not substantially degraded or deformed by exposure to ozone sterilant for a period of time and under conditions sufficient to sterilize the device.

16. The device of claim 1, wherein a portion of the scraping edge is crenate.

17. A method for removing infected tissue, wherein said method comprises using the device of claim 1 to remove infected tissue from a patient.

18. The method of claim 17, wherein said infected tissue is removed by:
    scraping an infected site on or in the patient with the scraping edge of the curette head of the device of any one of claims 1 through 16 to dislodge infected tissue at an infected site;
    flowing an irrigation liquid out of the seventh opening to create a liquid suspension of the dislodged tissue; and
    applying a negative pressure to the eighth opening to evacuate the liquid suspension from the infected site.

* * * * *